US012805856B2

(12) United States Patent
Foley et al.

(10) Patent No.: US 12,805,856 B2
(45) Date of Patent: Nov. 24, 2026

(54) MEDICAL DEVICES FOR USE IN THE CREATION OF A TEMPORARY PNEUMOPERITONEUM

(71) Applicant: Core Access Surgical Technologies, Inc., Atlanta, GA (US)

(72) Inventors: Glenn Foley, New York, NY (US); Oscar Jimenez, New York, NY (US)

(73) Assignee: Core Access Surgical Technologies, Inc., Atlanta, GA (US)

(*) Notice: Subject to any disclaimer, the term of this patent is extended or adjusted under 35 U.S.C. 154(b) by 839 days.

(21) Appl. No.: 18/030,499

(22) PCT Filed: Oct. 6, 2020

(86) PCT No.: PCT/US2020/054415

§ 371 (c)(1),
(2) Date: Apr. 5, 2023

(87) PCT Pub. No.: WO2022/075977

PCT Pub. Date: Apr. 14, 2022

(65) Prior Publication Data

US 2023/0364358 A1 Nov. 16, 2023

(51) Int. Cl.
*A61B 17/02* (2006.01)
*A61B 1/32* (2006.01)
(Continued)

(52) U.S. Cl.
CPC ............ *A61B 17/0281* (2013.01); *A61B 1/32* (2013.01); *A61B 17/0218* (2013.01);
(Continued)

(58) Field of Classification Search
CPC ..... A61B 17/02; A61B 17/30; A61B 17/0218; A61B 1/32; A61B 17/34; A61B 90/40;
(Continued)

(56) References Cited

U.S. PATENT DOCUMENTS 4,633,865 A 1/1987 Hengstberger et al.
6,315,770 B1 11/2001 de la Torre et al.
(Continued)

FOREIGN PATENT DOCUMENTS

EP 2168509 B1 * 8/2012 ............. A61B 18/14
GB 2526603 A * 12/2015 ............... A61L 2/22
(Continued)

OTHER PUBLICATIONS

International Search Report and Written Opinion mailed Dec. 29, 2020 in PCT/IB2020/054415 (9 pgs.).
(Continued)

*Primary Examiner* — Cris L. Rodriguez
(74) *Attorney, Agent, or Firm* — Quicker Law, LLC

(57) ABSTRACT

Medical devices for use in the creation of a temporary pneumoperitoneum include a rigid dome, a sealing element, a retaining band, a septum, and a vacuum port. The rigid dome includes first and second dome sections. The first dome section engages with the second dome section to form the rigid dome. The retaining band applies a force to secure the first dome section relative to the second dome section. The sealing element seals the first and second dome sections. The septum engages at an aperture between the first and second dome sections. The vacuum port connects a vacuum source to the rigid dome to reduce a pressure on an interior of the rigid dome.

18 Claims, 16 Drawing Sheets

(51) Int. Cl.
*A61B 17/00* (2006.01)
*A61B 17/34* (2006.01)
*A61M 13/00* (2006.01)

(52) U.S. Cl.
CPC .................... *A61B 17/3423* (2013.01); *A61B 2017/00561* (2013.01); *A61M 13/003* (2013.01)

(58) Field of Classification Search
CPC ............ A61B 17/0281; A61B 17/3423; A61B 17/3462; A61B 17/3474; A61B 17/3403; A61B 2017/306; A61B 2017/308; A61B 2017/00428; A61B 2017/00907; A61B 2017/00561; A61B 2017/00566; A61B 2017/3407; A61B 2017/3419; A61B 2017/3445; A61B 90/02; A61B 2017/3492; A61M 1/0066; A61M 13/003; A61M 39/0247; A61M 17/0218
See application file for complete search history.

(56) References Cited

U.S. PATENT DOCUMENTS

| | | | | |
|---|---|---|---|---|
| 7,585,281 | B2 * | 9/2009 | Nezhat | A61B 17/3403 604/23 |
| 8,382,654 | B2 | 2/2013 | Taylor | |
| 8,425,410 | B2 | 4/2013 | Murray et al. | |
| 8,845,682 | B2 | 9/2014 | Penner et al. | |
| 8,876,708 | B1 | 11/2014 | Piskun et al. | |
| 10,722,227 | B2 * | 7/2020 | Foley | A61B 17/30 |
| 10,799,267 | B2 | 10/2020 | McFarlane | |
| 2002/0019639 | A1 | 2/2002 | Dorn | |
| 2002/0137982 | A1 * | 9/2002 | Taylor | A61B 17/00 600/37 |
| 2004/0049127 | A1 | 3/2004 | Nezhat | |
| 2004/0267202 | A1 | 12/2004 | Potter | |
| 2006/0079921 | A1 * | 4/2006 | Nezhat | A61B 17/3403 604/23 |
| 2007/0270745 | A1 * | 11/2007 | Nezhat | A61B 5/6834 604/115 |
| 2008/0058603 | A1 * | 3/2008 | Edelstein | A61B 17/3403 600/201 |
| 2008/0058851 | A1 * | 3/2008 | Edelstein | A61B 17/3415 606/185 |
| 2008/0262527 | A1 * | 10/2008 | Eder | A61B 17/3403 606/185 |
| 2009/0082633 | A1 | 3/2009 | Kathrani et al. | |
| 2010/0030032 | A1 * | 2/2010 | Voegele | A61F 2/0063 600/210 |
| 2010/0081882 | A1 * | 4/2010 | Hess | A61B 17/3423 600/245 |
| 2013/0197315 | A1 | 8/2013 | Foley | |
| 2015/0133738 | A1 * | 5/2015 | Foley | A61B 17/3423 600/204 |
| 2016/0302826 | A1 | 10/2016 | Prati | |
| 2017/0056064 | A1 * | 3/2017 | Zergiebel | A61B 17/3474 |
| 2019/0175164 | A1 | 6/2019 | Taylor et al. | |
| 2020/0222039 | A1 | 7/2020 | Foley | |
| 2020/0268410 | A1 * | 8/2020 | Yaari | A61B 17/3439 |
| 2021/0161553 | A1 * | 6/2021 | Lin | A61B 90/10 |
| 2021/0205589 | A1 * | 7/2021 | Dong | A61M 27/002 |
| 2022/0265259 | A1 * | 8/2022 | Jimenez | A61B 17/0281 |
| 2023/0414091 | A1 * | 12/2023 | Foley | A61B 17/0281 |

FOREIGN PATENT DOCUMENTS

| | | | | | |
|---|---|---|---|---|---|
| RU | 2604780 | C2 | | 12/2016 | |
| WO | WO-2009015030 | A1 | * | 1/2009 | A61B 17/3403 |

OTHER PUBLICATIONS

Partial English-language translation of Office Action mailed Jul. 1, 2025 in Brazil Application No. 112023006342-6 (3 pgs.).
Office Action mailed Jul. 27, 2025 in Israel Application No. 301967 (6 pgs.).
Office Action mailed May 28, 2024 in Japan Application No. 2023-520554 with English-language translation (7 pgs.).
English-language translation of Office Action mailed Jan. 21, 2025 in Japan Application No. 2023-520554 (4 pgs.).
Office Action mailed Aug. 20, 2025 in Korea Application No. 10-2023-7015416 with English-language translation (18 pgs.).
Office Action mailed Oct. 7, 2025 in Mexico Application No. MX/a/2023/003937 with English-language translation (14 pgs.).
Office Action mailed Apr. 25, 2024 in Russia Application No. 2023106500 with English-language translation (22 pgs.).
International Search Report and Written Opinion mailed Mar. 18, 2021 in PCT/US2020/065095 (8 pgs.).
Office Action mailed Sep. 21, 2025 in Israel Application No. 301943 (5 pgs.).
English-language translation of Office Action mailed Sep. 3, 2024 in Japan Application No. 2023-545727 (5 pgs.).
English-language translation of Decision to Grant mailed Jan. 7, 2025 in Japan Application No. 2023-545727 (3 pgs.).
Office Action mailed Aug. 20, 2025 in Korea Application No. 10-2023-7015417 with English-language translation (7 pgs.).
Office Action mailed Oct. 8, 2025 in Mexico Application No. MX/a/2023/003938 with English-language translation (14 pgs.).
Office Action mailed Apr. 25, 2024 in Russia Application No. 2023107209 with English-language translation (26 pgs.).
Office Action mailed Mar. 25, 2026 in India Application No. 202317031962 (12 pgs.).
Hayden, J.A. et al. "A hermetically sealed, fluid-filled surgical enclosure for microgravity". Aviation, Space, and Environmental Medicine, vol. 84, No. 12, 2013 (Abstract only).
Greenberg, J.A. "LapCap™", Reviews in Obstetrics & Gynecology, 2008, vol. 1, No. 2, pp. 84-85.
Office Action received May 4, 2026 in Mexico Application No. MX/a/2023/003937 with English-language translation (20 pgs.).
Office Action received May 4, 2026 in Mexico Application No. MX/a/2023/003938 with English-language translation (22 pgs.).
Office Action mailed Jun. 24, 2026 in Israel Application No. 301967 (4 pgs.).
Notice of Allowance mailed Jun. 24, 2026 in Israel Application No. 301943 (3 pgs.).
Notice of Allowance mailed Jun. 29, 2026 in Korean Appl. 10-2023-7015417 with English-language Translation (12 pgs.).
Office Action received Sep. 2, 2026 in Mexico Application No. MX/a/2023/003938 with English-language translation (16 pgs.).
Office Action received Sep. 2, 2026 in Mexico Application No. MX/a/2023/003937 with English-language translation (20 pgs.).

* cited by examiner

MEDICAL DEVICES FOR USE IN THE CREATION OF A TEMPORARY PNEUMOPERITONEUM

CROSS-REFERENCE TO RELATED APPLICATION

This application is a national stage application, filed under 35 U.S.C. § 371, of International Patent Application No. PCT/US20/54415, filed on Oct. 6, 2020, which is incorporated by reference herein in its entirety.

BACKGROUND

A laparoscopic surgical procedure is often preferred to a laparotomy due to shorter recovery times and the reduced adverse impact that it has on the patient's wellbeing. As part of the laparoscopic surgical procedure, a temporary pneumoperitoneum is formed in the patient's abdomen to separate the skin, tissue, and muscle from the organs in the abdominal cavity below. This is achieved by insufflating the patient's abdomen with an inert gas, usually carbon dioxide ($CO_2$) which is supplied via needle injection.

BRIEF DESCRIPTION OF DRAWINGS

The present description will be understood more fully when viewed in conjunction with the accompanying drawings of various examples of medical devices for use in the creation of a temporary pneumoperitoneum. The description is not meant to limit the medical devices to the specific examples. Rather, the specific examples depicted and described are provided for explanation and understanding of medical devices for use in the creation of a temporary pneumoperitoneum. Throughout the description the drawings may be referred to as drawings, figures, and/or FIGs.

DETAILED DESCRIPTION

Medical devices for use in the creation of a temporary pneumoperitoneum, as disclosed herein, will become better understood through a review of the following detailed description in conjunction with the figures. The detailed description and figures provide merely examples of the various embodiments of medical devices for use in the creation of a temporary pneumoperitoneum. Many variations are contemplated for different applications and design considerations; however, for the sake of brevity and clarity, all the contemplated variations may not be individually described in the following detailed description. Those skilled in the art will understand how the disclosed examples may be varied, modified, and altered and not depart in substance from the scope of the examples described herein.

Conventional devices restrict the movement of a medical apparatus inserted through the device into the patient's abdomen and allow little or no room for positional adjustment of the medical apparatus. Secondly, some of the known devices have a relatively complex construction which increases the cost of manufacture. As these devices are intended to be disposable, a low manufacturing cost is essential. Additionally, the complexity of conventional devices increases the learning curve as well as a risk of user error or device failure.

Implementations of the medical devices for use in the creation of a temporary pneumoperitoneum, as disclosed herein, may address some or all of the problems described above. For example, embodiments disclosed herein allow for adjustment and manipulate of the medical device relative to the surgical site and also allow for the maneuvering of medical apparatuses within the medical device while in place at the surgical site. Embodiments described herein also allow for removal of the medical device from the surgical site while allowing persistent use of an indwelling trocar line. In other words, the trocar need not be removed to remove the medical device from the surgical site. Additionally, the relative lack of complexity of the medical device reduces cost, potential user error, and failure rate of the medical device itself. For example, in many surgical operations, it is advantageous to leave a trocar or other medical apparatuses indwelling while removing the medical device to provide clear access for additional medical apparatuses to be introduced, laterally or otherwise, to the surgical site without interference from the medical device.

Figure 1:
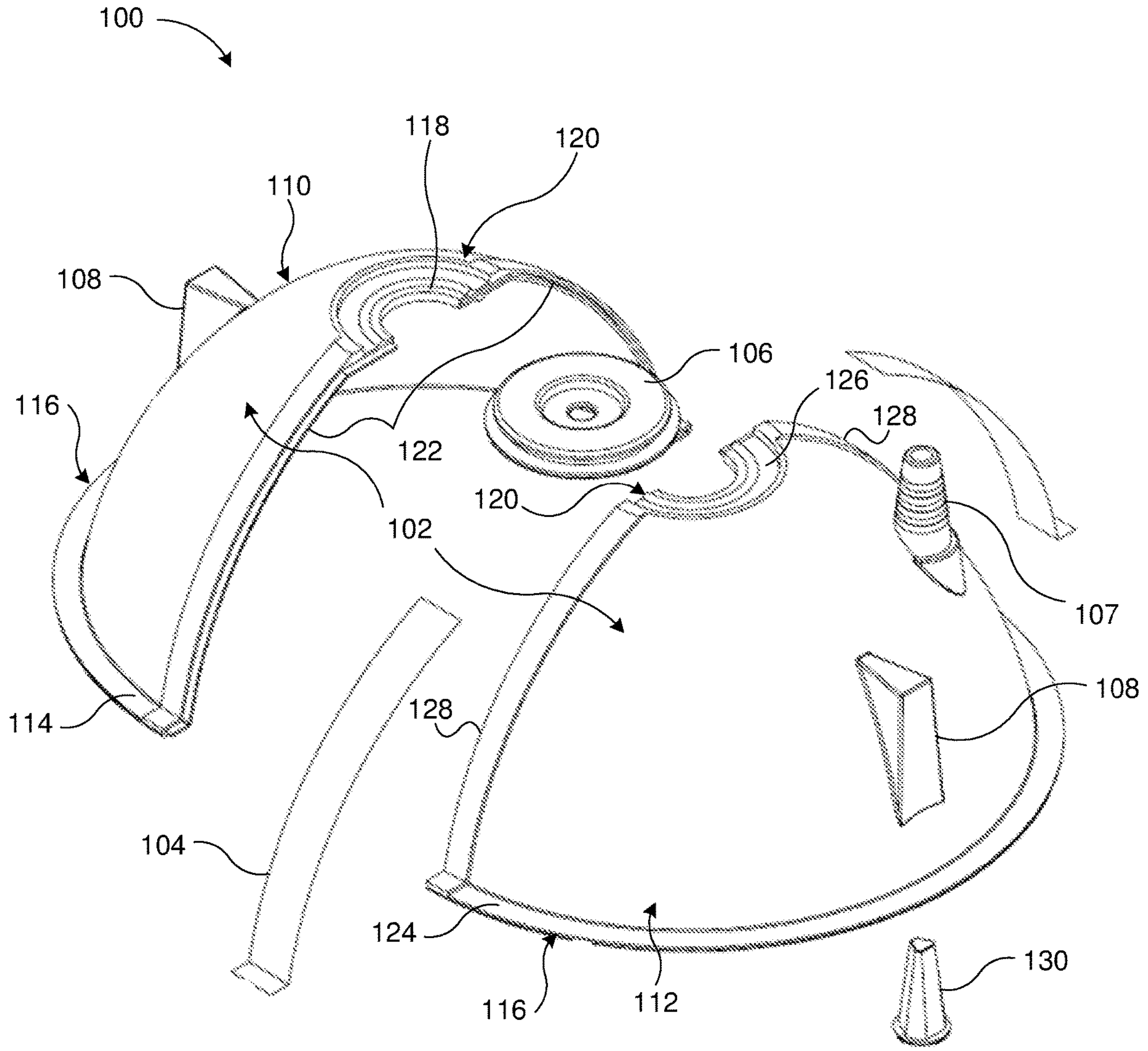
FIG. 1 illustrates an exploded view of a medical device for use in the creation of a temporary pneumoperitoneum, according to an embodiment.

FIG. 1 illustrates an exploded view of a medical device 100 for use in creating a temporary pneumoperitoneum, according to an embodiment. The use of a separable dome allows for creation of a temporary pneumoperitoneum to assist in preparation for and execution of surgery. The separability allows for removal of the dome while keeping a medical apparatus in place.

In some embodiments, the medical device 100 includes a rigid dome 102, a sealing element 104, a septum 106, a vacuum port 107, and a raised structure 108. The rigid dome 102 is an approximately substantially hemispherical or dome-shaped structure having a first dome section 110 and a second dome section 112. The first dome section 110 and the second dome section 112 form the rigid dome 102 when joined together. In other words, the first dome section 110 has a semi-hemispherical geometry or constitutes a portion of the hemispherical geometry of the rigid dome 102 while the second dome portion 112 has a semi-hemispherical geometry complimentary to the first dome section 112.

The first dome section 110 and the second dome section 112 may each form an equal half of the rigid dome 102. In some embodiments, one of the first dome section 110 or the second dome section 112 constitutes a greater portion of the rigid dome 102 that the other. In some embodiments, at least one of the first dome section 110 or the second dome section 112 is transparent or semi-transparent to facilitate viewing of a surgical site on an interior of the rigid dome 102. A radius of curvature of the first dome section 110 may be equivalent to a radius of curvature of the second dome section 112. In some embodiments, the curvature or other geometry of the first dome section 110 is different from a corresponding geometry in the second dome section 112.

In some embodiments, the first dome section 110 is wholly releasable from the second dome section 112 to allow for the rigid dome 102 to be removed and leave a medical apparatus, inserted through the rigid dome 102, to be left in place. In other embodiments, the first dome section 110 is partially releasable from the second dome section 112 and remains coupled to the second dome section 112 at, for example, a hinge, tether, joint, or so forth. In some embodiments, the remaining connection between the first dome section 110 and the second dome section 112 is further separable to fully separate the first dome section 110 from the second dome section 112. In other embodiments, the remaining connection between the first dome section 110 and the second dome section 112 is separation resistant. The first dome section 110 of the rigid dome 102 also includes a first patient interface portion 114 of a patient interface 116, a first aperture portion 118 of an aperture 120, and a first joining interface 122.

In some embodiments, the first patient interface portion 114 extends around a base of the first dome section 110. The first patient interface portion 114 may be rolled outward from the first dome section 110 to provide an increased surface area in the first patient interface portion 114 relative to a thickness of the first dome section 110. In some embodiments, the first patient interface portion 114 forms a first portion of the patient interface 116 which extends across both the first dome section 110 and the second dome section 112. The patient interface 116 may reduce a pressure at the surgical site around the rigid dome 102. This may reduce impact to the flow of blood or other fluids or reduce the risk of tissue damage. Additionally, the increased surface area at the patient interface 116 may reduce a risk of exacerbating a wound at the surgical site. In some embodiments, the patient interface 116 may include a coating, liner, treatment, or so forth to improve sanitization, traction, vacuum seal, or so forth.

The first aperture portion 118 forms a portion of an aperture 120 that is opposite the first patient interface portion 114 on the first dome section 110. In some embodiments, the aperture 120 is a circular opening in the rigid dome 102. In other embodiments, the aperture 120 has a non-circular geometry. In some embodiments, the aperture 120 is formed, in equal parts, by both the first dome section 110 and the second dome section 112. In other embodiments, the aperture 120 is formed, in greater degree, by one of the first dome section 110 and the second dome section 112 that the other of the first dome section 110 and the second dome section 112. The aperture 120 may include ridges, depressions, rings, friction fittings, and so forth to improve a seal, retention, releasability, or other characteristics in relation to the septum 106.

In some embodiments, the first joining interface 122 extends along an edge of the first dome section 110 between the first aperture portion 118 and the first patient interface portion 114. In some embodiments, the first joining interface 122 forms a flange, lip, tongue or groove, ledge, or so forth. In some embodiments, the first joining interface 122 is configured to align with the second joining interface 128 to join the first dome section 110 to the second dome section 112 to form the rigid dome 102.

The second dome section 112 of the rigid dome 102 includes a second patient interface portion 124, a second aperture portion 126, and a second joining interface 128. In some embodiments, the second patient interface portion 124 compliments the first patient interface portion 114 to form the entirety of the patient interface 116. In some embodiments, the first patient interface portion 114 forms a portion of the patient interface 116 which extends around a base of the second dome section 112. In some embodiments, the second patient interface portion 124 is rolled outward from the second dome section 112 to provide increased surface area in the second patient interface portion 124 relative to a thickness of the second dome section 112.

The second aperture portion 126 is positioned opposite the second patient interface portion 124 second dome section 112. In some embodiments, the second aperture portion 126 combines with the first aperture portion 118 of the first dome section 110 to form the aperture 120. The second aperture portion 126 may constitute a greater or lesser amount of the aperture 120 relative to the first aperture portion 118. In some embodiments, one or both of the first aperture portion 118 and the second aperture portion 126 includes an alignment feature to correspond with a geometry or feature of the septum 106 to facilitate alignment of the septum within the aperture 120.

In some embodiments, the second joining interface 128 extends along an edge of the second dome section 112 between the second aperture portion 126 and the second patient interface portion 124. The second joining interface 128 may be configured to couple to the first joining interface 122 to join the first dome section 110 to the second dome section 112 to form the rigid dome 102.

In some embodiments, a sealing element 104 is configured to removably seal the first joining interface 122 of the first dome section 110 to the second joining interface 128 of the second dome section 112. In some embodiment, the sealing element 104 is a medical tape. In some embodiments, the sealing element 104 applied to the exterior of the rigid dome 102 to overlap the first joining interface 122 and the second joining interface 128 to seal the first joining interface 122 to the second joining interface 128. The sealing element 104 may be removable from at least one of the first joining interface 122 or the second joining interface 128 to at least partially separate the first dome section 110 from the second dome section 112.

In other embodiments, the sealing element 104 is a low shear strength adhesive. For example, the low shear strength adhesive may be a low shear strength silicon or other low shear strength polymer breakable by hand. The sealing element 104 may be removeable to facilitate separation of the first dome section 110 from the second dome section 112. The sealing effect provided by the sealing element 104 allows for a reduction in leakage of pressure to or from the interior of the rigid dome 102 when the rigid dome 102 is in place at the surgical site. In some embodiments, the sealing element 104 includes a tab, strip, handle, loop, or so forth, to facilitate removal of the sealing element 104 from the rigid dome 102

In some embodiments, the medical device 100 also includes a septum 106. The septum 106 may be positioned within the aperture 120 and form a permeable barrier to allow a medical apparatus to penetrate through the septum 106 to access the interior of the rigid dome 102. The septum 106 may be configured to engage with the first aperture portion 118 of the first dome section 110 and engage with the second aperture portion 126 of the second dome section 112. In some embodiments, the septum 106 is formed from a different material than the rigid dome 102. The use of a different material may allow for easier puncture of the septum 106 relative to the rigid dome 102, thereby facilitating insertion of the medical apparatus through the septum 106.

The medical device 100 may also include a vacuum port 107. In some embodiments, the vacuum port 107 is disposed in the rigid dome 102 between the patient interface 116 and the aperture 120. In some embodiments, the vacuum port 107 forms a fluid pathway between an interior of the rigid dome 102 and an exterior of the rigid dome 102. In some embodiments, the vacuum port 107 facilitates connection of a vacuum source to the rigid dome 102 to reduce a pressure on the interior of the rigid dome 102. In some embodiments, the vacuum port 107 projects outward from the rigid dome 102 in a vertical or angled orientation. The vacuum port 107 may be smooth, threaded, barbed, or so forth, to accept a connection to the vacuum source.

Some embodiments include a vacuum port plug 130. The vacuum port plug 130 may be compatible with the vacuum port 107 to form a barrier at the vacuum port 107 to maintain a reduced pressure on the interior of the rigid dome 102. In some embodiments, the vacuum port plug 130 may be incorporated into the vacuum port 107 to create a one-way valve allowing air to be evacuated from the interior of the rigid dome 102 while resisting the flow of air back into the interior of the rigid dome 102. In some embodiments, the vacuum port plug 130 is actuated by an input on the exterior of the rigid dome 102 to equalize the pressure on the interior of the rigid dome 102 to an exterior pressure.

The medical device 100 may also include a raised structure 108 extending outward from an exterior surface of the rigid dome 102 to form a physical interface to receive a force to physically manipulate the rigid dome 102. For example, a user may grasp the medical device 100 at the raised structure 108 to position the medical device 100 relative to the surgical site, orient the medical device 100 relative to the user or the surgical site, apply a force into or away from a plane of the surgical site, separate the first dome section 110 from the second dome section 112, or so forth. In some embodiments, the raised structure 108 includes grip elements. For example, the raised structure 108 may include ridges, knurling, dimples, coatings, or so forth to increase a friction coefficient of at least a portion of the raised structure 108.

Figure 2:
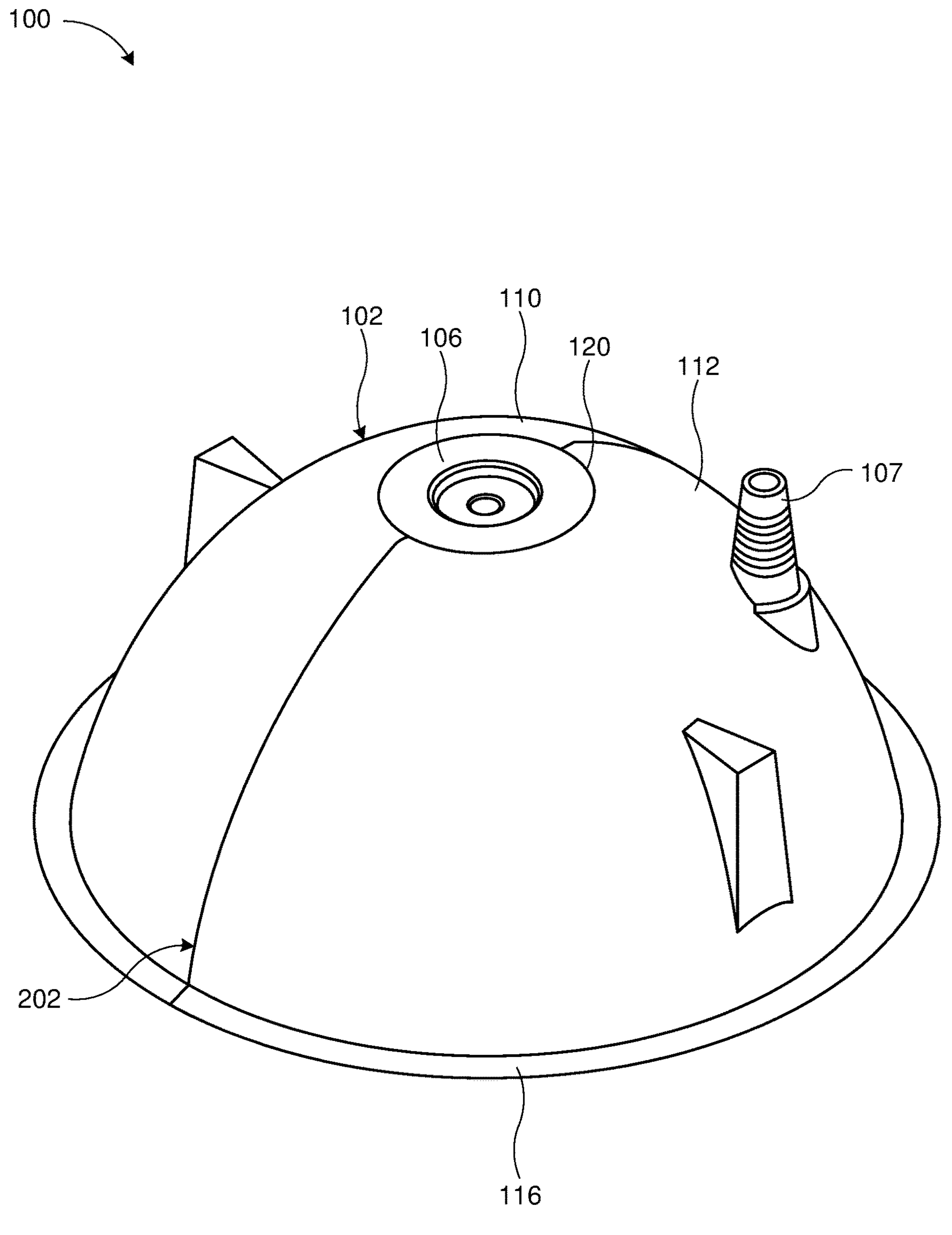
FIG. 2 illustrates an assembled view of the medical device of FIG. 1, according to an embodiment.

FIG. 2. illustrates an assembled view of the medical device 100 of FIG. 1, according to an embodiment. Some embodiments forms a complete air-tight or near air-tight dome to cover and manipulate a surgical site to reduce risk of unintended harm during a surgical operation or in preparation for a surgical operation. In some embodiments, the first dome section 110 seals to the second dome section 112 to create a closed seam 202. In some embodiments, the seam 202 is sealed with an adhesive or other material applied within the seam 202. In other embodiments, the seam 202 is sealed with a tape or other material applied to an exterior of the seam 202 on an exterior of the rigid dome 102 or an interior of the rigid dome 102.

In some embodiments, the septum 106 is sealed in the aperture 120 of the rigid dome 102. In some embodiments, the septum 106 is sealed within the aperture 120 using a material similar to or differing from a material applied at the seam 202. In other embodiments, a structure of the septum 106 is sufficient to maintain a seal relative to the aperture 120.

Figure 3:
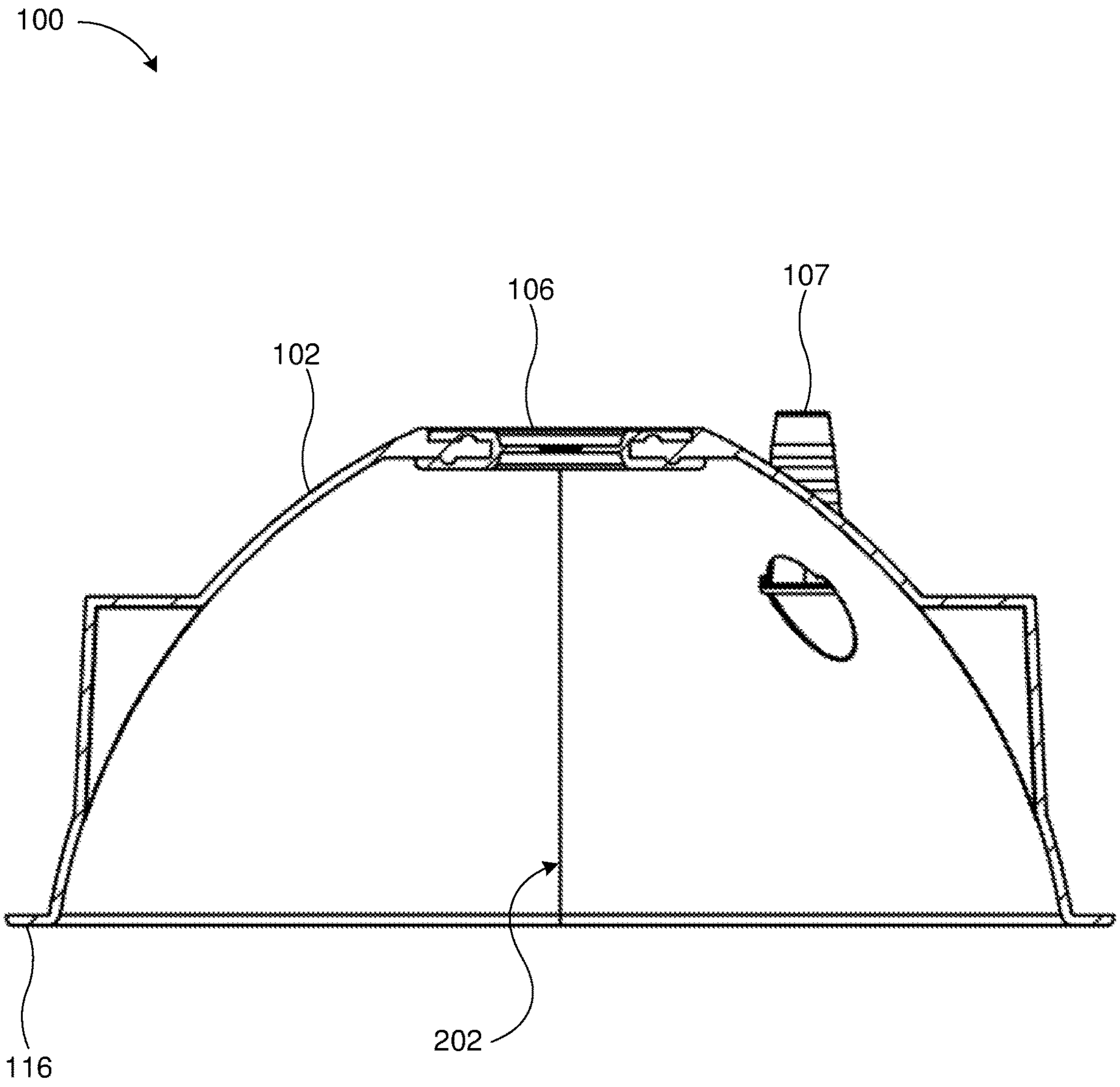
FIG. 3 illustrates a cross-sectional view of the medical device of FIG. 1, according to an embodiment.

FIG. 3 illustrates a cross-sectional view of the medical device 100 of FIG. 1, according to an embodiment. Some embodiments shows a pass-through aspect of the vacuum port 107 into an interior of the medical device 100 which allows pressure to be reduced on the interior of the medical device 100 to draw a surgical site up into the interior of the medical device 100 to reduce risk of unintended harm at a surgical site. In some embodiments, the vacuum port 107 extends from the rigid dome 102 in a substantially vertical orientation. In other embodiments, the vacuum port 107 extends from the rigid dome 102 at an angle perpendicular relative to the surface of the rigid dome 102 from which the vacuum port 107 extends. In other embodiments, other angles may be used to facilitate connection with a vacuum source, reduce interference with access to the septum 106, or so forth. In some embodiments, the vacuum port 107 is positioned on the rigid dome 102 to reduce the likelihood of drawing, distending, deflecting, or otherwise moving, tissue at the surgical site to, or into, the vacuum port 107.

Figure 4:
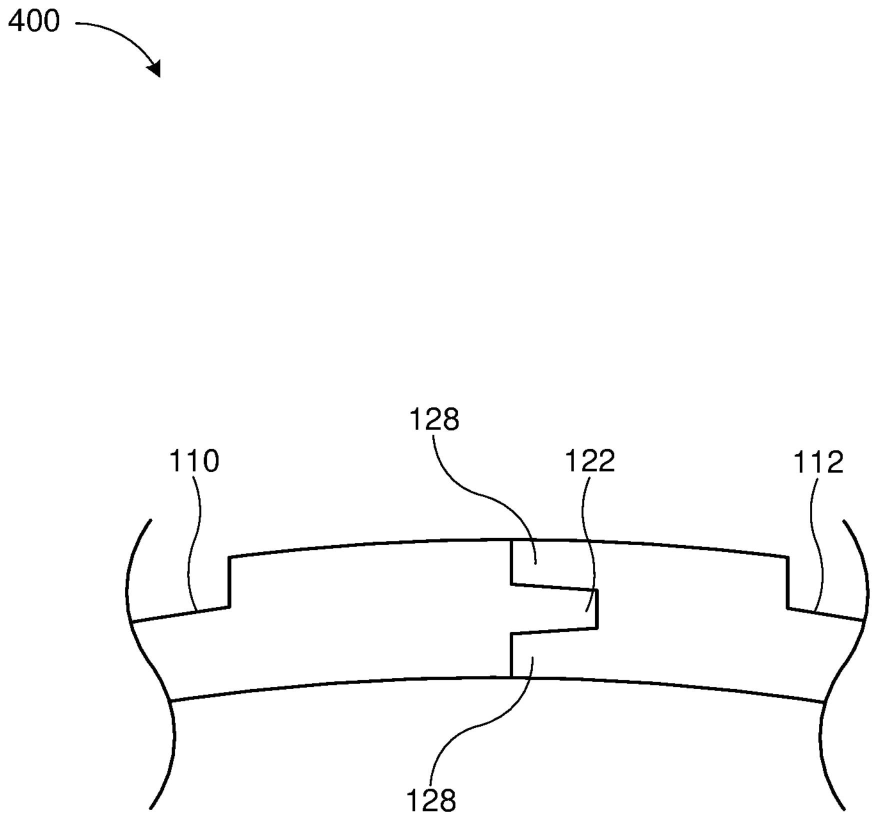
FIG. 4 illustrates a cross-sectional view of a joint of the medical device of FIG. 1, according to an embodiment.

FIG. 4 illustrates a cross-sectional view of a joint 400 of the medical device of FIG. 1, according to an embodiment. In some embodiments, the first joining interface 122 is configured to contact the second joining interface 128 to form a seal. In some embodiments, the joint 400 is a tongue-and-groove joint with the first joining interface 122 inserting into a groove forming the second joining interface 128. In other embodiments, the joint 400 is a lap joint, a sunk lap joint, a butt joint, a t-bull joint, a flange joint, a standing joint, a flat lock joint, or so forth.

Figure 5:
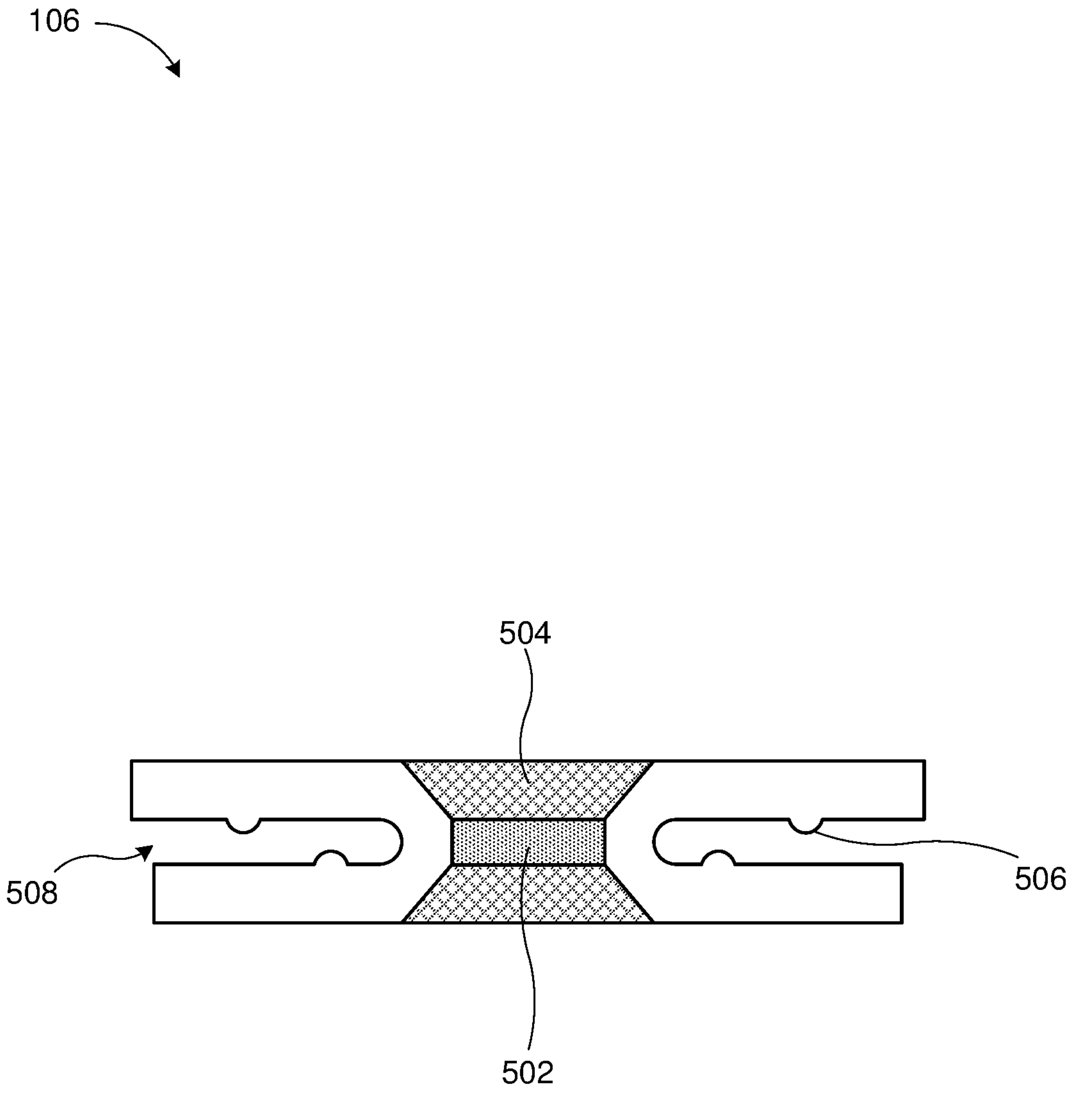
FIG. 5 illustrates a cross-sectional view of a septum of the medical device of FIG. 1, according to an embodiment.

FIG. 5 illustrates a cross-sectional view of the septum 106 of the medical device 100 of FIG. 1, according to an embodiment. In some embodiments, the septum 106 includes an access structure 502 through which a medical apparatus accesses an interior of the rigid dome 102. In some embodiments, the access structure 502 of the septum 106 is thinner than another part of the septum 106. The reduced thickness of the access structure 502 may allow for easier penetration of the septum 106 at the access structure 502. In some embodiments, the access structure 502 includes a material that is different from another material in the remainder of the septum 106. For example, the access structure 502 may include a softer or more elastic material that is not included in the remainder of the septum 106 or is included at a lower quantity or concentration.

Additionally, the reduced thickness of the septum 106 at the access structure 502 may provide a visual indicator of the location at which the medical apparatus may be inserted through the septum 106 with reduced chance of impacting the medical apparatus on the rigid dome 102. In some embodiments, the access structure 502 is positioned centrally on the septum 106 forming a recess 504 other either side of the access structure 502. In other embodiments, the access structure 502 may be positioned off-center forming recesses 504 of different sizes or only a single recess on one side of the septum 106 with the access structure 502 being flush to a remainder of the septum 106 on one side of the septum 106.

In some embodiments, the septum 106 includes a retaining structure 506 to apply a retaining force at the aperture 120. In some embodiments, the retaining structure 506 includes raised portions within a channel 508 extending around at least a portion of a perimeter of the septum 106. The retaining structure 506 may be rings formed in the channel 508. The retaining structure 506 may be rounded, squared, beveled, or so forth.

Figure 6:
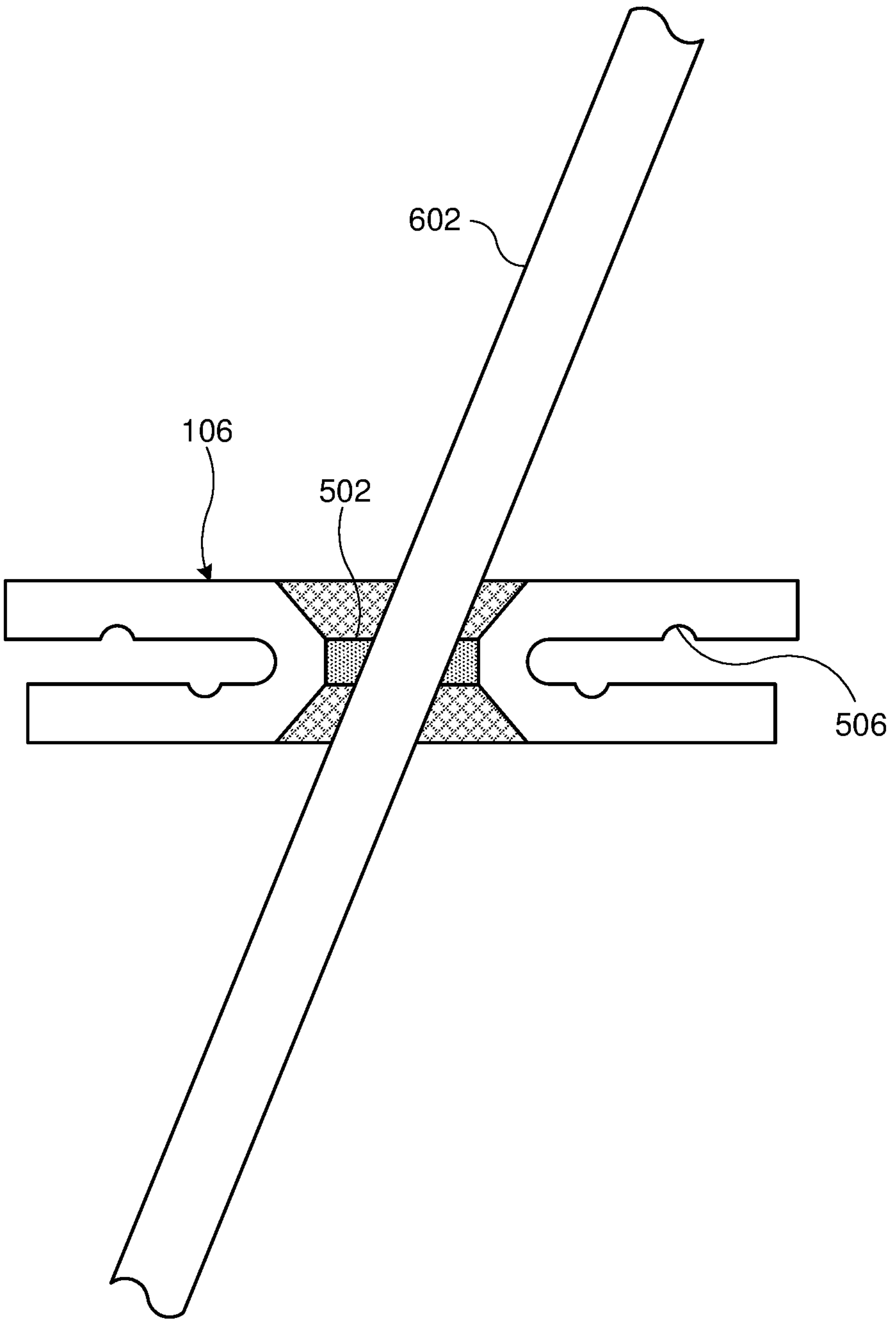
FIG. 6 illustrates a cross-sectional view of the septum of the medical device of FIG. 1 with a medical apparatus inserted, according to another embodiment.

FIG. 6 illustrates a cross-sectional view of the septum 106 of the medical device 100 of FIG. 1 with a medical apparatus 602 inserted, according to another embodiment. In some embodiments, the medical apparatus 602 is inserted through the access structure 502 of the septum 106 to gain access to an interior of the medical device 100. As illustrated, embodiments of the septum 106 allow for the medical device 100 to inserted at a range of angles as may be occasioned by the surgical site, type of surgical operation, or other variables. In some embodiments, the septum 106 is configured to accept insertion of the medical apparatus 602 at a first angle and maintain a seal at the medical apparatus through a transition to a second angle different from the first angle to allow for repositioning of the medical apparatus 602. Also shown is a variation of the retaining structure 506 which is recessed. The recessed retaining structure 506 interfaces with a corresponding raised structure on the rigid dome 102 at the aperture 120.

Figure 7:
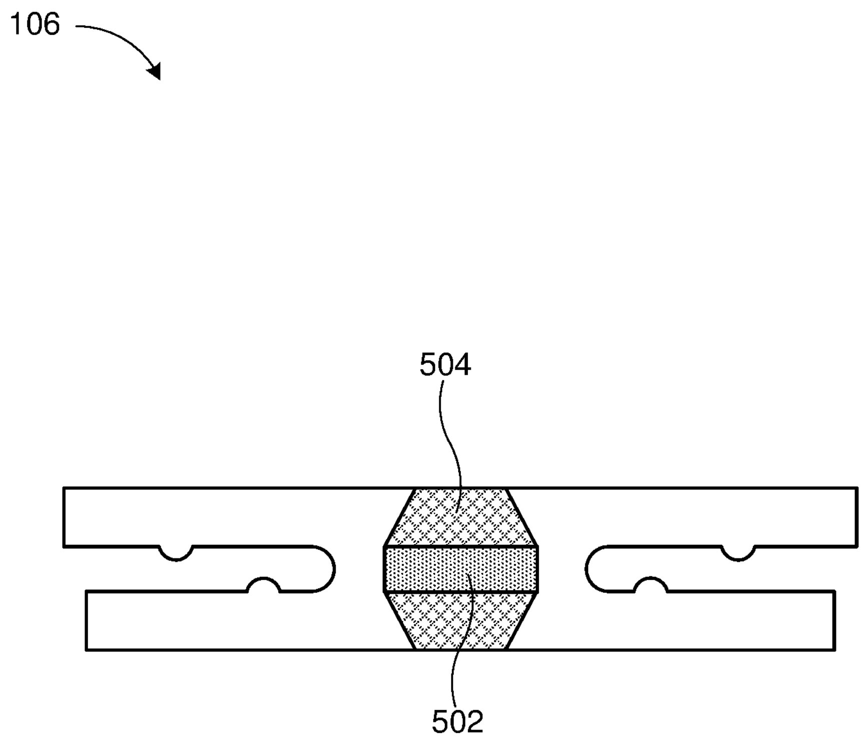
FIG. 7 illustrates a cross-sectional view of the septum of the medical device of FIG. 1, according to another embodiment.

FIG. 7 illustrates a cross-sectional view of the septum 106 of the medical device 100 of FIG. 1, according to another embodiment. In some embodiments, the septum 106 may include a recess 504 with an opening that is narrowed at a surface of the septum 106. In some embodiments, the narrowed aspect of the recess 504 may provide a self-righting force applied to the medical apparatus 602 as the medical apparatus 602 is inserted into the access structure 502 of the septum 106.

Figure 8:
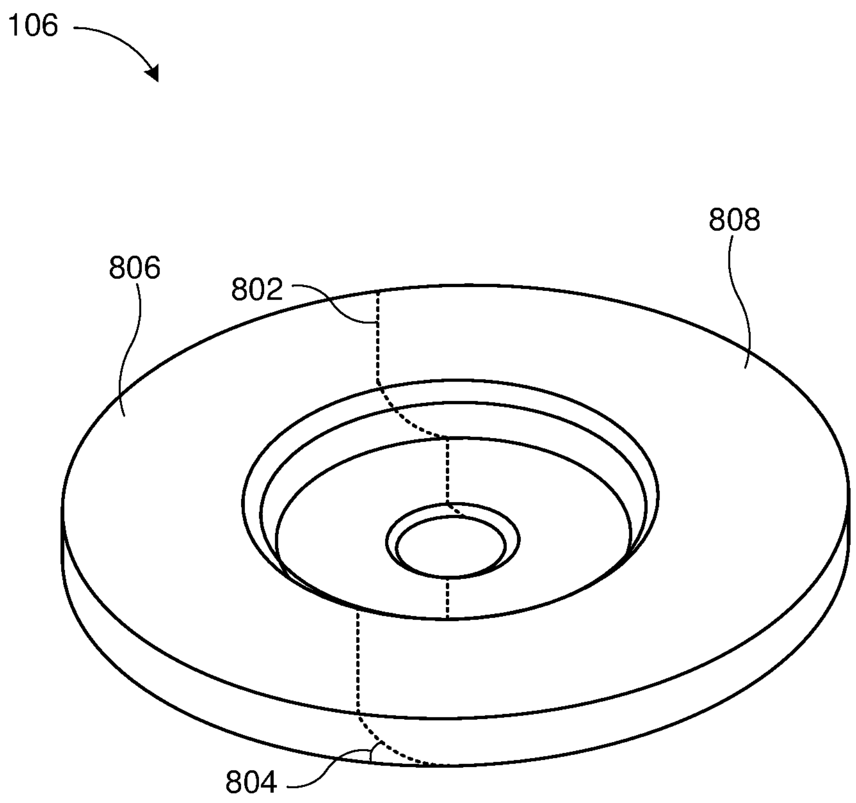
FIG. 8 illustrates a perspective view of the septum of the medical device of FIG. 1, according to another embodiment.

FIG. 8 illustrates a cross-sectional view of the septum 106 of the medical device 100 of FIG. 1, according to another embodiment. In some embodiments, a separable embodiment of the septum 106 is shown which allows for the septum 106 to be removed without disturbing or removing the medical apparatus 602 from the surgical site. In other words, the septum 106 is at least partially separable to release from the medical apparatus 602 without removing the medical apparatus 602 from the surgical site. This can reduce a risk of unintended harm or increase a likelihood of success of the surgical operation. In some embodiments, the septum 106 is separable at a separation boundary 802 formed in the septum 106. The separation boundary 802 may include a perforation, a different material, a siping or cut, or other weakening or tear facilitating structure or variation. The separation boundary 802 may be at some boundary angle 804 relative to a surface of the septum 106. For example, the separation boundary 802 may have a boundary angle 804 of 30-degrees. In some embodiments, the separation boundary 802 is a through-cut which is maintained together in a sealed arrangement by the material of the septum 106, a reduced pressure within the rigid dome, and/or a force applied to the septum 106 by the rigid dome 102. In some embodiments, the septum 106 may be divided into a first septum portion and second portion at the separation boundary 802. In other embodiments, the septum 106 may be partially divided from a center of the septum 106 out to an edge of the septum 106.

Figure 9:
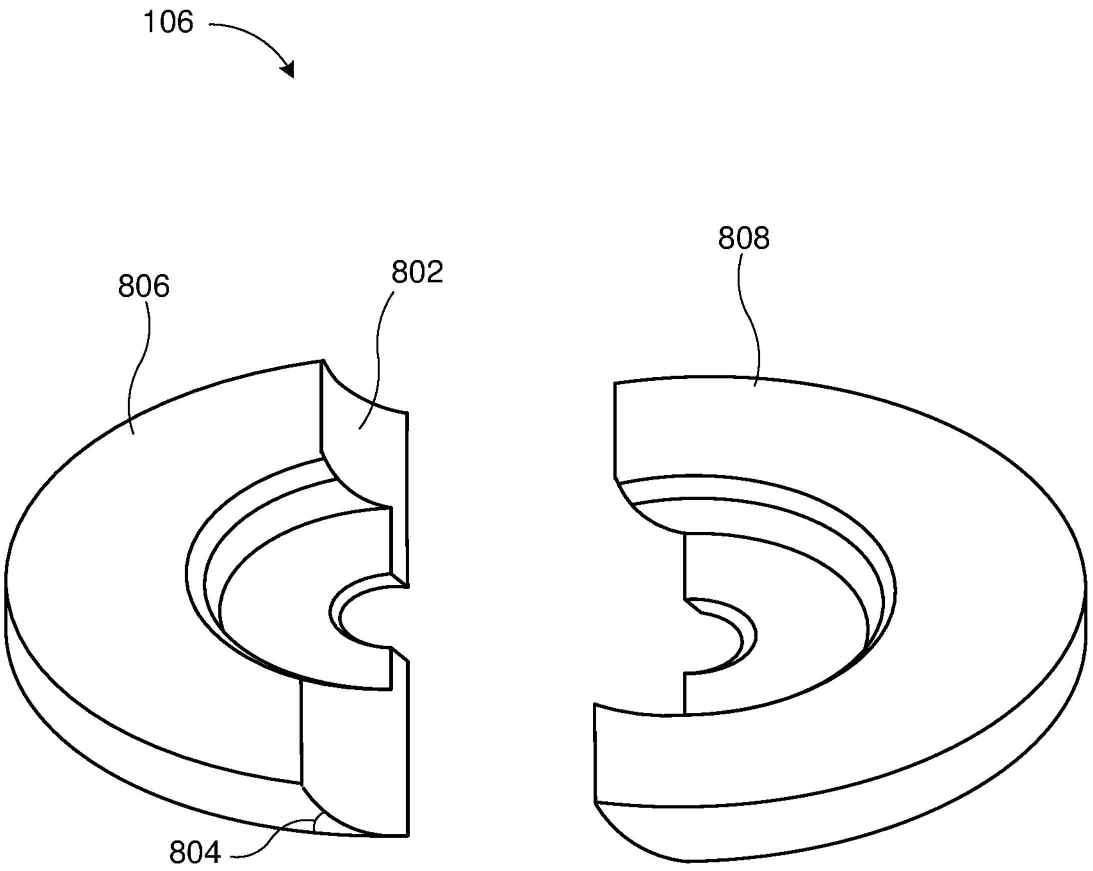
FIG. 9 illustrates a perspective view of the septum of FIG. 8 in a separated arrangement, according to another embodiment.

FIG. 9 illustrates a perspective view of the septum 106 of FIG. 8 in a separated arrangement, according to another embodiment. In some embodiments, the septum 106 is separated into distinct pieces in the first septum portion 806 and the second septum portion 808. While the first septum portion 806 is shown as being similar in size and quantity of the septum 106 as the second septum portion 808, other embodiments may incorporate a different size ratio for the first septum portion 806 and the second septum portion 808.

Figure 10:
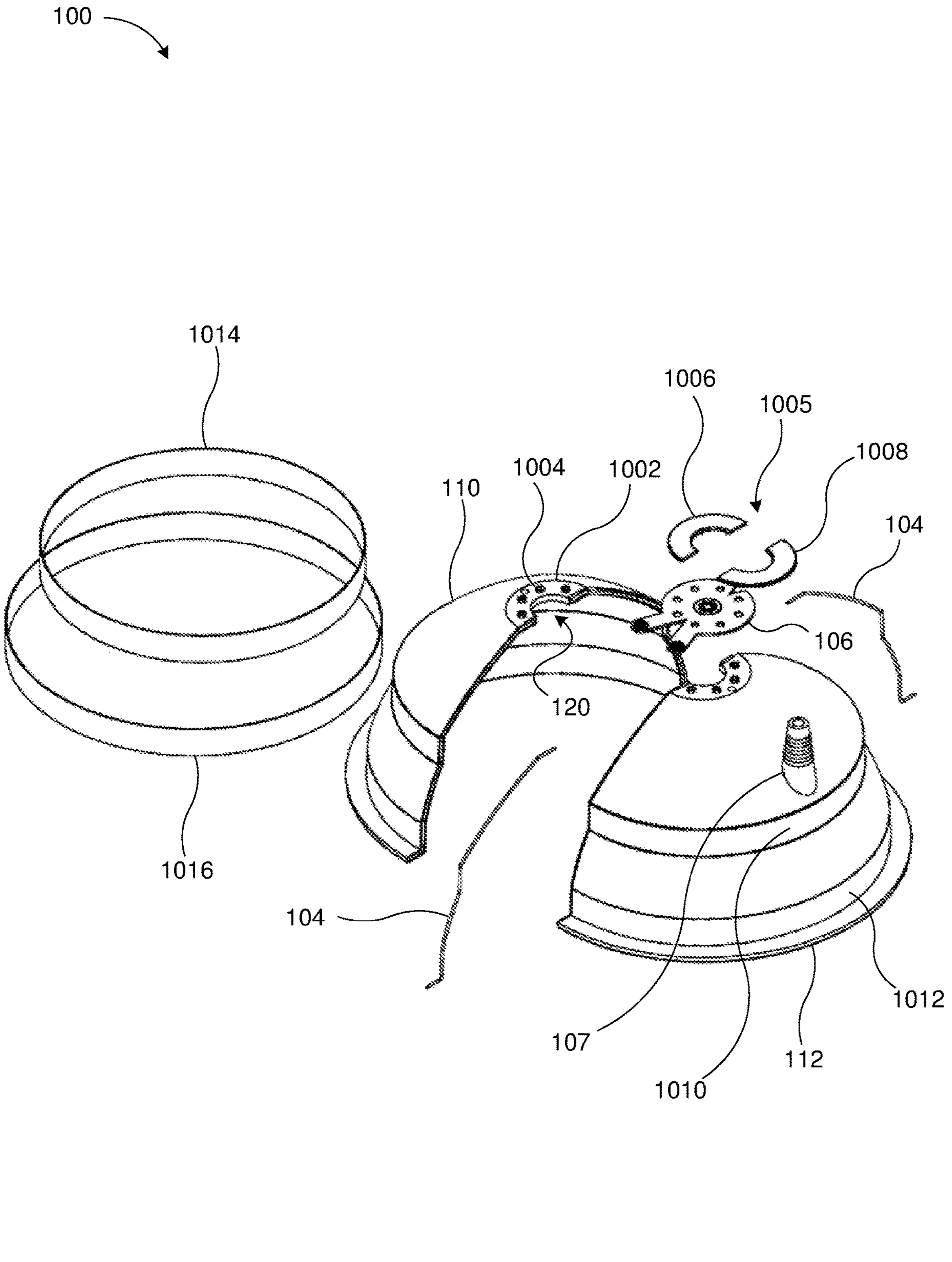
FIG. 10 illustrates an exploded view of a medical device, according to an embodiment.

FIG. 10 illustrates an exploded view of a medical device 100, according to an embodiment. Some embodiments of the medical device 100 allow for a medical professional to form a temporary pneumoperitoneum at a surgical site using an available vacuum source and without causing undue complication or risk for the patient while significantly reducing a risk of unintended damage or harm during a surgical operation. In some embodiments, the medical device 100 includes a first dome section 110 and a second dome section 112 having a first band region 1010 shaped to accommodate a first retaining band 1014 and a second band region 1012 shaped to accommodate a second retaining band 1016. The first band region 1010 extends around both the first dome section 110 and the second dome section 112. The first band region 1010 may be sized and oriented to form a parallel cylinder with the first band region 1010 being untampered to retain the first retaining band 1014. In other embodiments, the first band region 1010 may be tapered towards a top or bottom of the medical device 100. The second band region 1012 may be configured similar to or different from the first band region 1010. In some embodiments, the first band region 1010 is smaller in diameter than the second band region 1012 to accommodate a smaller diameter in the first retaining band 1014 relative to the second retaining band 1016. In some embodiments, the vacuum port 107 is disposed between the first band region 1010 and the aperture 120. In some embodiments, the vacuum port 107 may be disposed between the first band region 1010 and the second band region 1012. Other embodiments include other arrangement of the vacuum port 107. In some embodiments, the first retaining band 1014 or the second retaining band 1016 is a shrink band having a sufficient tensile strength. In other embodiments the first retaining band 1014 or the second retaining band 1016 is a reinforced tape. In some embodiments, the reinforced tape may be self-adhesive. The reinforced tape may include reinforcing elements such as carbon filaments, nanotubes, glass fibers, polymers, and so forth. In some embodiments, the reinforcement may be axial or biaxial.

In some embodiments, the medical device 100 includes a septum seat 1002. The septum seat 1002 may be formed around the aperture 120 to facilitate placement and securing of the septum 106. In some embodiments, the septum seat 1002 is a planar region formed around the aperture 120 on each of the first dome section 110 and the second dome section 112. The septum seat 1002 may be annular in geometry and concentric with the aperture 120. In other embodiments, the septum seat 1002 may have other shapes and may have other alignments relative to the aperture 120.

In some embodiments, the septum seat 1002 includes retention holes 1004 extending into a thickness of the first dome section 110 and the second dome section 112. In some embodiments, the retention holes 1004 extend completely through the thickness of the first dome section 110 and the thickness of the second dome section 112 to an interior of the medical device 100. In other embodiments, the retention holes 1004 do not extend completely through the thickness of the first dome section 110 and the thickness of the second dome section 112.

The retention holes 1004 may facilitate securing of the septum 106 into place on the septum seat 1002. In some embodiments, the medical device 100 further includes a retention ring 1005 which may be configured to engage with the retention holes 1004 to secure the septum 106 at the septum seat 1002. In some embodiments, the retention ring 1005 is separable into a first ring portion 1006 and a second ring portion 1008. The separability of the retention ring 1005 may allow for removal of the medical device 100 from around a medical tool such as a trocar, needle, line, or so forth. The retention ring 1005 may be separated into the first ring portion 1006 and the second ring portion 1008 or may require mechanical separation via tearing, cutting, or so forth.

In some embodiments, the medical device 100 includes a sealing element 104 that is pre-shaped to conform to a cross-sectional geometry of the joint between the first dome portion 110 and the second dome portion 112. The sealing element 104 may include a resilient material or a crushable material. For example, the sealing element 104 may include a polymer material, fluoropolymer, silicone rubber, (solid strand or tubing) to form an O-ring style seal or the sealing element 104 may be a metallic, wax, or other crushable seal material to form a gasket style seal. Other sealing methodologies may also be implemented.

Figure 11:
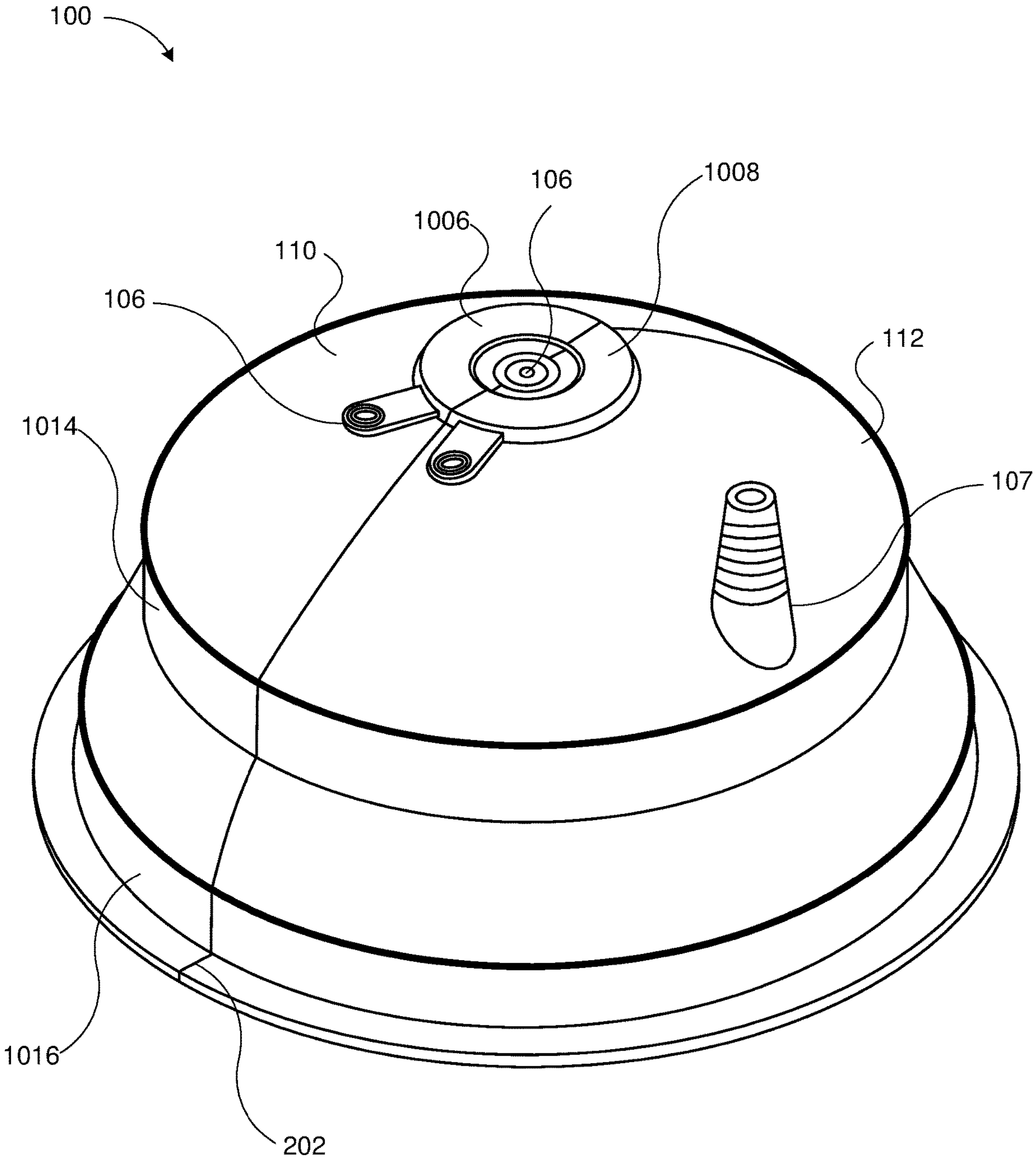
FIG. 11 illustrates a perspective view of the medical device of FIG. 10, according to an embodiment.

FIG. 11 illustrates a perspective view of the medical device 100 of FIG. 10, according to an embodiment. Some embodiments allows for a secure seal to be formed around a surgical site to create a temporary pneumoperitoneum to reduce the risk of unintentional harm. Additionally, the medical device 100 is removable while leaving medical instruments in-situ at the surgical site further reducing potential harm from withdrawal and reinsertion.

In some embodiments, the first retaining band 1014 and the second retaining band 1016 are positioned to retain the first dome portion 110 closed with the second dome portion 112. The first retaining band 1014 and the second retaining band 1016 may be removed by cutting or otherwise severing to remove from the medical device 100 and facilitate separation of the first dome portion 110 from the second dome portion 112 at the joint 202.

Figure 12:
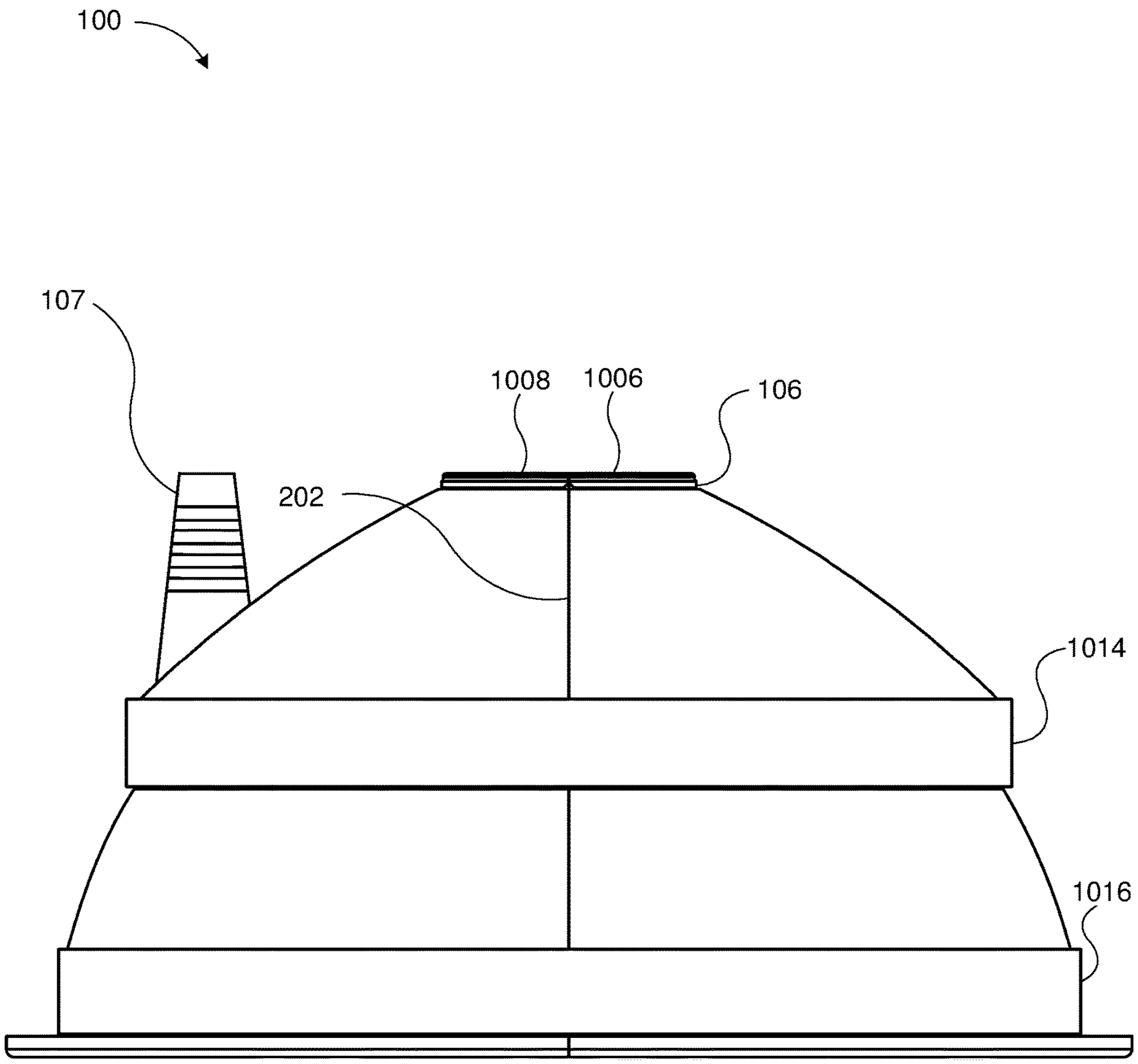
FIG. 12 illustrates a side view of the medical device of FIG. 10, according to an embodiment.

FIG. 12 illustrates a side view of the medical device of FIG. 10, according to an embodiment. Some embodiments forms a comfortable and easily deployable structure which provides the ability to form the temporary pneumoperitoneum without additional harm to the patient.

In some embodiments, the first retaining band 1014 is positioned near a middle of the medical device 100 while the second retaining band 1016 is positioned near a bottom of the medical device 100. In some embodiments, the first retaining band 1014 and the second retaining band 1016 may apply the same amount or similar retaining force on the medical device 100 to keep the joint 202 sealed. In other embodiments, the first retaining band 1014 may apply more or less force than does the second retaining band 1016 which may be based on a position, thickness, material, or other characteristic or component of the first retaining band 1014 or the second retaining band 1016.

Figure 13:
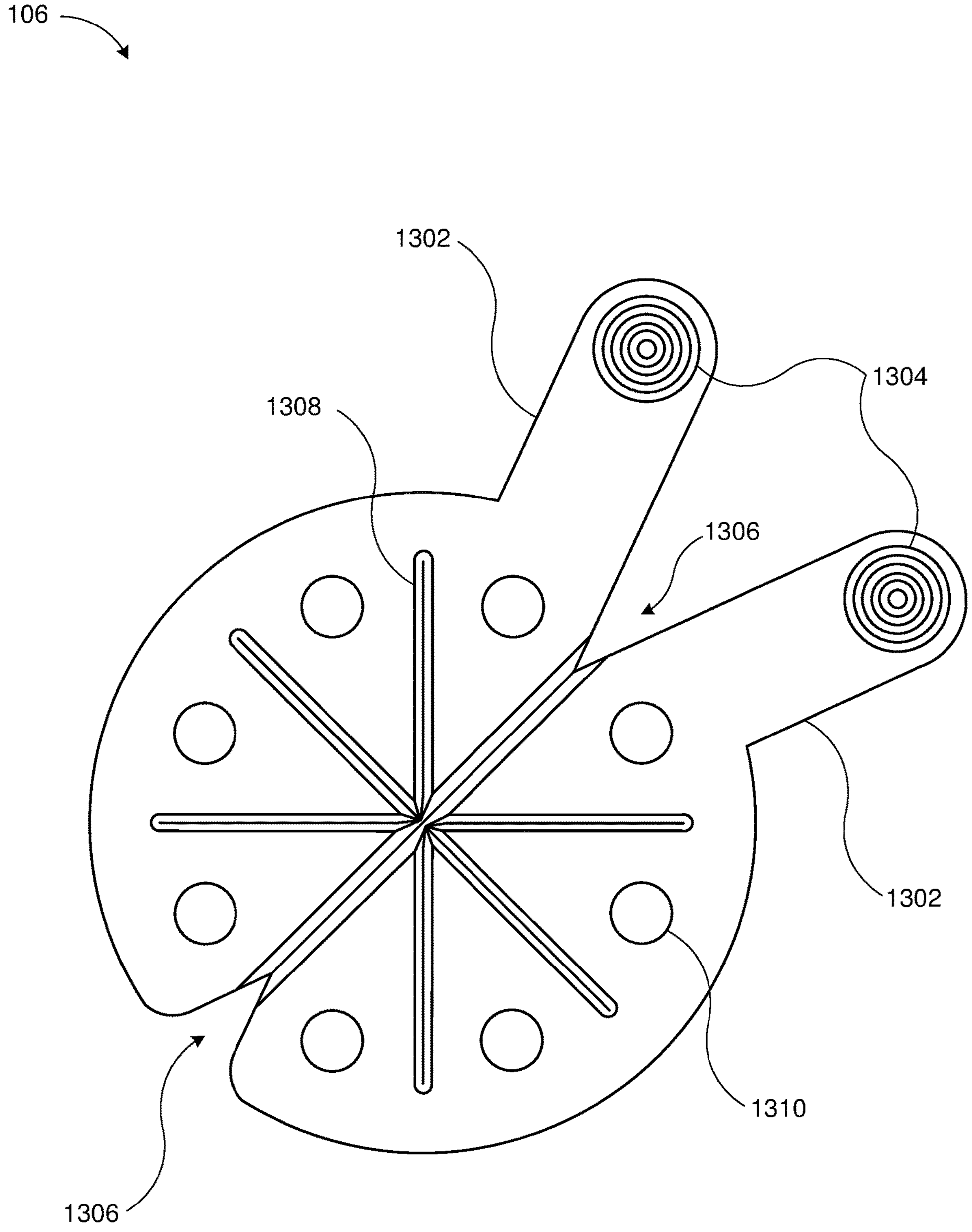
FIG. 13 illustrates a bottom view of the septum of the medical device of FIG. 10, according to an embodiment.

FIG. 13 illustrates a bottom view of the septum 106 of the medical device of FIG. 10, according to an embodiment. Some embodiments of the septum 106 allows for insertion of a medical instrument while maintaining a vacuum-resilient seal on the medical instrument. The septum 106 is also able to separate to allow for removal of the septum 106 from the medical instrument without withdrawing the medical instrument from the surgical site.

In some embodiments, the septum 106 includes grip tabs 1302. The grip tabs 1302 extend from the septum 106 at an angle from each other to form a location for a surgeon, or other medical personnel, to grip the septum 106. The grip tabs 1302 may include textured portions 1304 to improve grip. This may help to improve grip in the presence of blood, fats, oils, irrigation fluids, and so forth.

In some embodiments, the septum 106 includes a series of tear lines 1308 formed in the structure of the septum 106 to facilitate separation of the septum 106. The tear lines 1308 may coincide with tear notches 1306 or other designed failure points to control a position, direction, or mode of failure or tearing of the septum 106 to prevent unwanted fragmentation or a tear which does not fully separate the septum 106 to release a medical instrument inserted therethrough.

In some embodiments, the septum 106 includes alignment holes 1310. The alignment holes 1310 may be through-holes formed in the septum 106 to facilitate alignment and securing of the septum 106 in conjunction with the septum seat 1002 and the retention ring 1005. For example, the retention ring may be aligned to protrude through the alignment holes 1310 of the septum 106 and into the retention holes 1004 formed in the septum seat 1002.

Figure 14:
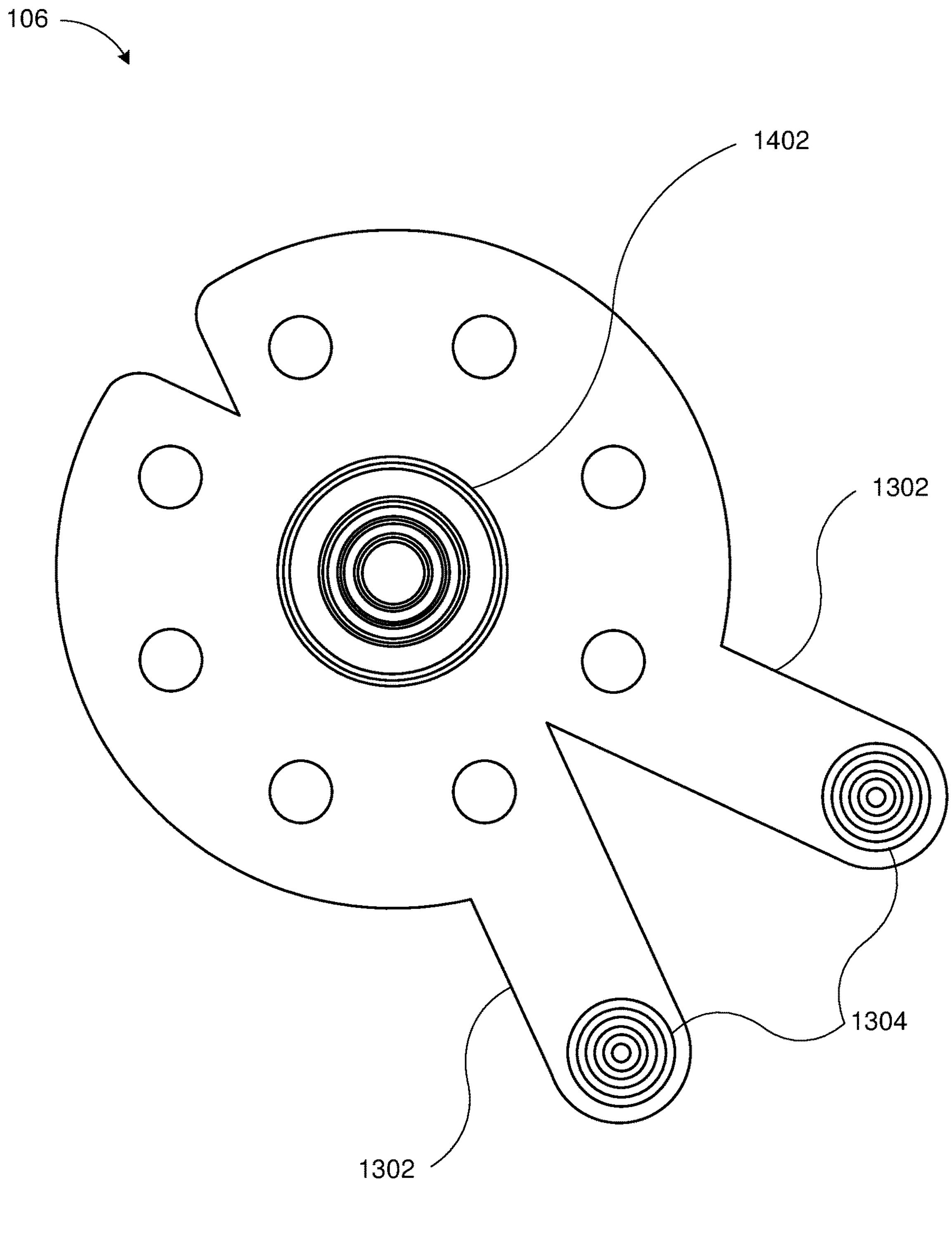
FIG. 14 illustrates a top view of the septum of the medical device of FIG. 10, according to an embodiment.

FIG. 14 illustrates a top view of the septum 106 of the medical device of FIG. 10, according to an embodiment. Some embodiments provides a readily useable septum 106 with both a seal texture 1402 forming a target for insertion of a medical instrument reducing difficulty of use and forming a flexible seal accepting a wide range of medical instrument sizes while maintaining seal.

In some embodiments, the seal texture 1402 is formed as a raised structure disposed in a center of the septum 106. The raised structure of the seal texture 1402 may form a ring to readily accept medical instruments with a round cross-section. Other shapes are contemplated to accommodate non-round cross-sections.

Figure 15:
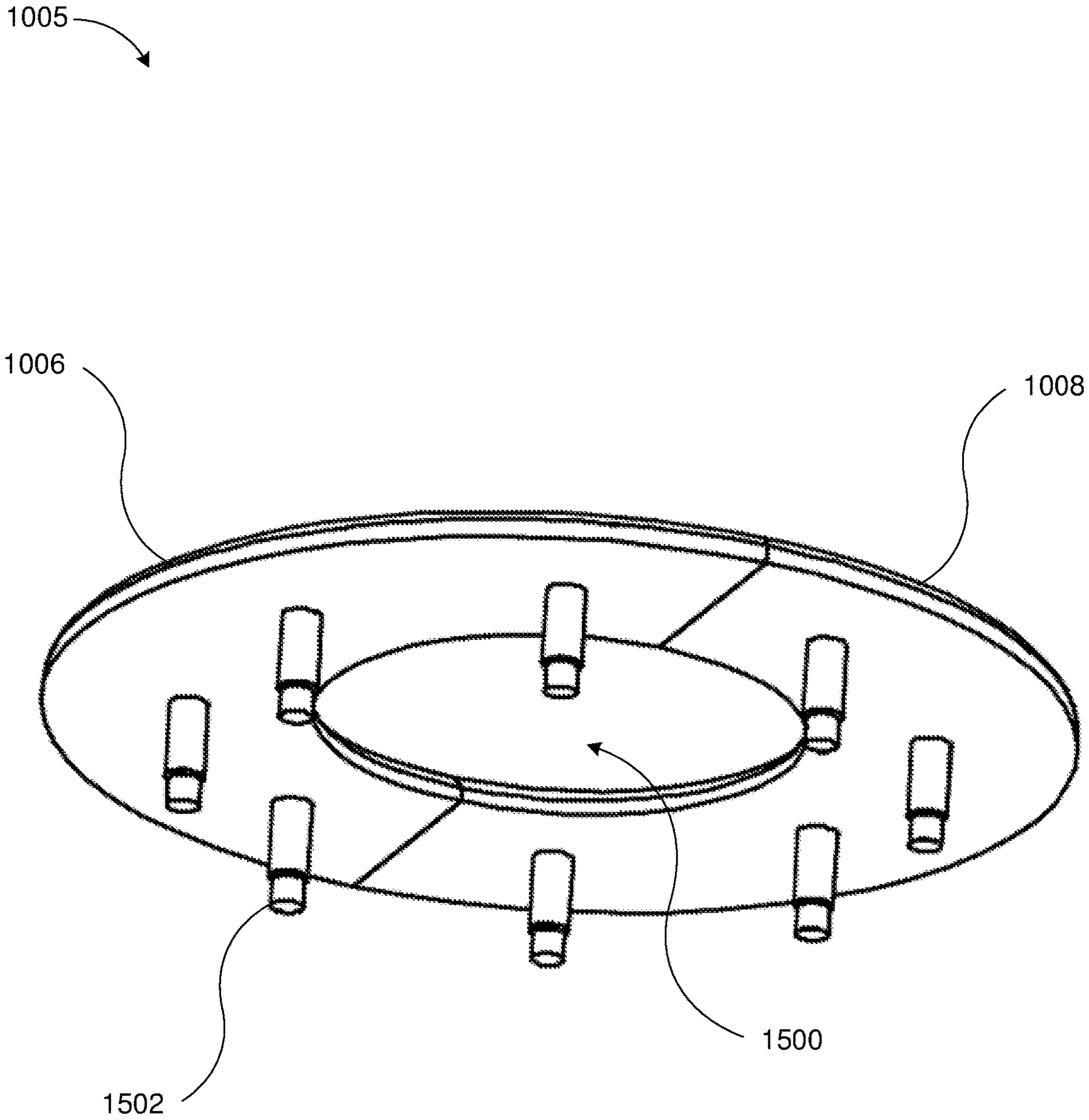
FIG. 15 illustrates a perspective view of a retention ring of the medical device of FIG. 10, according to an embodiment.

FIG. 15 illustrates a perspective view of a retention ring 1005 of the medical device of FIG. 10, according to an embodiment. Some embodiments of the retention ring 1005 allow for increased security and seal of the septum 106 relative to the first dome portion 110 and the second dome portion 112 while also allowing for removal from a medical instrument while the instrument remains in-situ. The retention ring 1005 may be separable into a first ring portion 1006 and a second ring portion 1008. The retention ring 1005 may be separated into the first ring portion 1006 and the second ring portion 1008 or may facilitate user input to separate the retention ring 1005. The retention ring 1005 may include a central aperture 1500. The central aperture 1500 may be positioned in the retention ring 1005 to allow access to the septum 106 for insertion of a medical instrument through the septum 106.

In some embodiments, the retention ring 1005 includes posts 1502 extending perpendicular from a plane of the retention ring 1005. In some embodiments, the posts 1502 are arranged in a pattern around the retention ring 1005. In some embodiments, the posts 1502 are distributed evenly around the retention ring 1005. In some embodiments, the posts 1502 retain the septum 106 to facilitate splitting of the septum 106 in response to separation of the first dome section 110 and the second dome section 112.

In some embodiments, the posts 1502 may have a consistent cross-sectional geometry. In other embodiments, the posts 1502 have a differential geometry. For example, in some embodiments, the posts 1502 have a tip section with a smaller diameter. This variation in geometry may allow the posts 1502 to engage separately with the septum 106 and the retention holes 1004 of the septum seat 1002. The posts 1502 may provide alignment of the retention ring 1005 relative to the first dome section 110 and the second dome section 112 and alignment of the septum 106 with the first dome section 110 and the second dome section 112.

Figure 16:
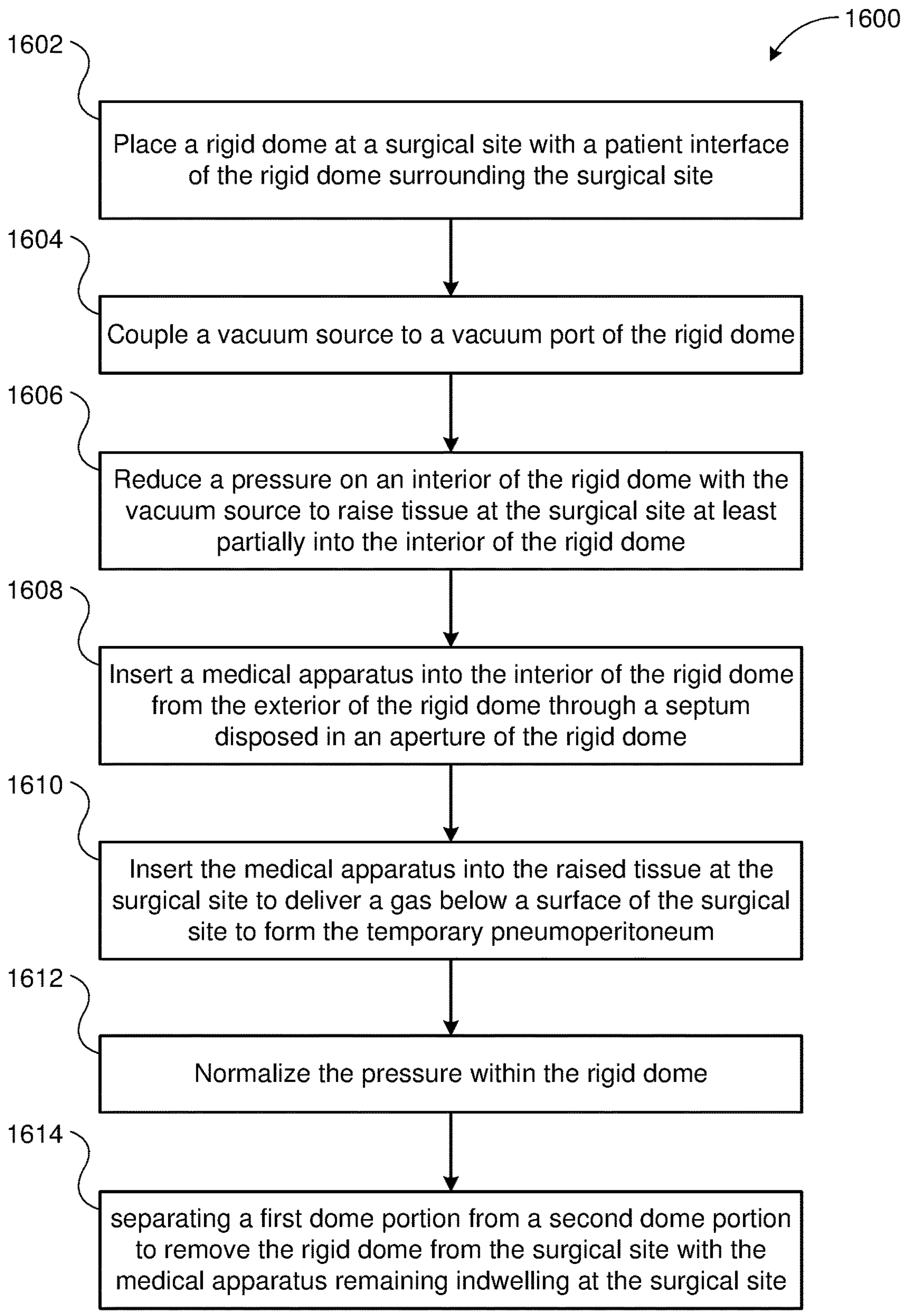
FIG. 16 illustrates a flow diagram of a method for using the medical device of FIG. 1, according to another embodiment.

FIG. 16 illustrates a flow diagram of a method 1600 for using the medical device 100 of FIG. 1, according to another embodiment. The method 1600 allows for creation of a temporary pneumoperitoneum for surgery. The method 1600 may include placing a rigid dome at a surgical site with a patient interface of the rigid dome surrounding the surgical site. For example, the rigid dome 102 may be placed at a surgical site with the patient interface 116 of the rigid dome 102 positioned to surround the surgical site (Block 1602).

The method 1600 may include coupling a vacuum source to a vacuum port of the rigid dome Block 1604). For example, a vacuum source may be coupled to the vacuum port 107 of the rigid dome 102 to supply a reduced pressure to the rigid dome 102. The method 1600 may include reducing a pressure on an interior of the rigid dome with the vacuum source to raise tissue at the surgical site at least partially into the interior of the rigid dome (Block 1606). For example, as the pressure within the rigid dome 102 is reduced, the tissue at the surgical site under the rigid dome will distend upward into the rigid dome 102.

The method 1600 may include inserting a medical apparatus into the interior of the rigid dome from the exterior of the rigid dome through a septum disposed in an aperture of the rigid dome (Block 1608). For example, the medical apparatus 602 may be inserted through the septum 106 of the rigid dome 102 to access an interior of the rigid dome 102. The method 1600 may include inserting the medical apparatus into the raised tissue at the surgical site to deliver a gas below a surface of the surgical site to form the temporary pneumoperitoneum (Block 1610). For example, the medical apparatus 602 may be introduced into the surgical site, which is distended into the rigid dome 102, to deliver an inert gas (e.g. $CO_2$) below a surface layer of the surgical site to create a temporary pneumoperitoneum at the surgical site to facilitate laparoscopic surgery or another surgical operation.

The method 1600 may include normalizing the pressure within the rigid dome (Block 912). For example, the pressure within the rigid dome 102 may be normalized or equalized by disengaging a vacuum source from the vacuum port 107, manipulating a vacuum port plug 130, lifting the rigid dome 102 from the surgical site, removing a sealing element 104, creating an initial separation between the first dome section 110 and the second dome section 112, or so forth. The method 1600 may include separating a first dome portion from a second dome portion to remove the rigid dome from the surgical site with the medical apparatus remaining indwelling at the surgical site (Block 1614). For example, the first dome section 110 may be separated from the second dome section 112 by grasping the raised structure 108 and applying a force to the rigid dome 102 to overcome a sealing element, removing the sealing element 104, or so forth.

A feature illustrated in one of the figures may be the same as or similar to a feature illustrated in another of the figures. Similarly, a feature described in connection with one of the figures may be the same as or similar to a feature described in connection with another of the figures. The same or similar features may be noted by the same or similar reference characters unless expressly described otherwise. Additionally, the description of a particular figure may refer to a feature not shown in the particular figure. The feature may be illustrated in and/or further described in connection with another figure.

Elements of processes (i.e. methods) described herein may be executed in one or more ways such as by a human, by a processing device, by mechanisms operating automatically or under human control, and so forth. Additionally, although various elements of a process may be depicted in the figures in a particular order, the elements of the process may be performed in one or more different orders without departing from the substance and spirit of the disclosure herein.

The foregoing description sets forth numerous specific details such as examples of specific systems, components, methods and so forth, in order to provide a good understanding of several implementations. It will be apparent to one skilled in the art, however, that at least some implementations may be practiced without these specific details. In other instances, well-known components or methods are not described in detail or are presented in simple block diagram format in order to avoid unnecessarily obscuring the present implementations. Thus, the specific details set forth above are merely exemplary. Particular implementations may vary from these exemplary details and still be contemplated to be within the scope of the present implementations.

Related elements in the examples and/or embodiments described herein may be identical, similar, or dissimilar in different examples. For the sake of brevity and clarity, related elements may not be redundantly explained. Instead, the use of a same, similar, and/or related element names and/or reference characters may cue the reader that an element with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be the same and/or similar to the specific portrayal of a related element in any given figure or example in order to share features of the related element.

It is to be understood that the foregoing description is intended to be illustrative and not restrictive. Many other implementations will be apparent to those of skill in the art upon reading and understanding the above description. The scope of the present implementations should, therefore, be determined with reference to the appended claims, along with the full scope of equivalents to which such claims are entitled.

The foregoing disclosure encompasses multiple distinct examples with independent utility. While these examples have been disclosed in a particular form, the specific examples disclosed and illustrated above are not to be considered in a limiting sense as numerous variations are possible. The subject matter disclosed herein includes novel and non-obvious combinations and sub-combinations of the various elements, features, functions and/or properties disclosed above both explicitly and inherently. Where the disclosure or subsequently filed claims recite "a" element, "a first" element, or any such equivalent term, the disclosure or claims is to be understood to incorporate one or more such elements, neither requiring nor excluding two or more of such elements.

As used herein "same" means sharing all features and "similar" means sharing a substantial number of features or sharing materially important features even if a substantial number of features are not shared. As used herein "may" should be interpreted in a permissive sense and should not be interpreted in an indefinite sense. Additionally, use of "is" regarding examples, elements, and/or features should be interpreted to be definite only regarding a specific example and should not be interpreted as definite regarding every example. Furthermore, references to "the disclosure" and/or "this disclosure" refer to the entirety of the writings of this document and the entirety of the accompanying illustrations, which extends to all the writings of each subsection of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an example described as including A, B, C, and D is an example that includes A, includes B, includes C, and also includes D. As used herein regarding a list, "or" forms a list of elements, any of which may be included. For example, an example described as including A, B, C, or D is an example that includes any of the elements A, B, C, and D. Unless otherwise stated, an example including a list of alternatively-inclusive elements does not preclude other examples that include various combinations of some or all of the alternatively-inclusive elements. An example described using a list of alternatively inclusive elements includes at least one element of the listed elements. However, an example described using a list of alternatively inclusive elements does not preclude another example that includes all of the listed elements. And an example described using a list of alternatively inclusive elements does not preclude another example that includes a combination of some of the listed elements. As used herein regarding a list, "and/or" forms a list of elements inclusive alone or in any combination. For example, an example described as including A, B, C, and/or D is an example that may include: A alone; A and B; A, B and C; A, B, C, and D; and so forth. The bounds of an "and/or" list are defined by the complete set of combinations and permutations for the list.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted examples.

The Applicant(s) reserves the right to submit claims directed to combinations and sub-combinations of the disclosed examples that are believed to be novel and non-obvious. Examples embodied in other combinations and sub-combinations of features, functions, elements and/or properties may be claimed through amendment of those claims or presentation of new claims in the present application or in a related application. Such amended or new claims, whether they are directed to the same example or a different example and whether they are different, broader, narrower or equal in scope to the original claims, are to be considered within the subject matter of the examples described herein.

The invention claimed is:

1. A medical device, comprising:

a rigid dome having a substantially hemispherical geometry configured to separate for removal from a surgical site to leave a medical apparatus in place at the surgical site, the rigid dome comprising:

a first dome section having a semi-hemispherical geometry forming a portion of the substantially hemispherical geometry of the rigid dome, wherein the first dome section comprises:

a first patient interface portion, of a patient interface, extending around a base of the first dome section, wherein the first patient interface portion extends outward away from the first dome section to provide increased surface area in the first patient interface portion relative to a thickness of the first dome section;

a first aperture portion of an aperture opposite the first patient interface portion on the first dome section; and a first joining interface extending along an edge between the first aperture portion and the first patient interface portion of the first dome section;

a second dome section having a semi-hemispherical geometry complementary to the first dome section, wherein the second dome section is configured to engage with the first dome section to form the rigid dome, the second dome section comprising:

a second patient interface portion, of the patient interface, extending around a base of the second dome section, wherein the second patient interface portion extends outward away from the second dome section to provide increased surface area in the second patient interface portion relative to a thickness of the second dome section;

a second aperture portion opposite the second patient interface portion on the second dome section; and a second joining interface extending along an edge of the second dome section between the second aperture portion and the second patient interface portion, wherein the second joining interface is configured to couple to the first joining interface to join the first dome section to the second dome section to form the rigid dome;

a retaining band configured to apply a retaining force to secure the first dome section relative to the second dome section, wherein the retaining band is positioned on a band region extending around both the first dome section and the second dome section;

a sealing element configured to removably seal the first joining interface of the first dome section to the second joining interface of the second dome section;

a septum positioned at the aperture and configured to engage with the first dome section at the first aperture portion and with the second dome section at the second aperture portion; and a vacuum port disposed in the rigid dome between the patient interface and the aperture, wherein the vacuum port forms a fluid pathway between an interior of the rigid dome and an exterior of the rigid dome, wherein the vacuum port facilitates connection of a vacuum source to the rigid dome to reduce a pressure on the interior of the rigid dome.

2. The medical device of claim 1, further comprising a vacuum port plug compatible with the vacuum port to form a barrier at the vacuum port to maintain the reduced pressure on the interior of the rigid dome.

3. The medical device of claim 1, wherein the sealing element comprises a medical tape applied to the exterior of the rigid dome to overlap the first joining interface and the second joining interface to seal the first joining interface to the second joining interface and removable from at least one of the first joining interface or the second joining interface to at least partially separate the first dome section from the second dome section.

4. The medical device of claim 1, wherein the sealing element comprises a low-shear strength adhesive configured to seal the first joining interface to the second joining interface and breakable to at least partially separate the first dome section from the second dome section.

5. The medical device of claim 1, further comprising a retention ring to apply a retaining force to the septum at the aperture.

6. The medical device of claim 5, wherein the septum is configured to provide a permeable barrier in the aperture to allow a medical apparatus to penetrate through the septum to access the interior of the rigid dome.

7. The medical device of claim 5, wherein the septum comprises an access structure formed within the septum and extending through a thickness of the septum to provide access to the interior of the rigid dome.

8. A method, comprising:

placing a rigid dome at a surgical site with a patient interface of the rigid dome surrounding the surgical site;

coupling a vacuum source to a vacuum port of the rigid dome;

reducing a pressure on an interior of the rigid dome with the vacuum source to raise tissue at the surgical site at least partially into the interior of the rigid dome;

inserting a medical apparatus into the interior of the rigid dome from an exterior of the rigid dome through a septum disposed in an aperture of the rigid dome;

inserting the medical apparatus into the raised tissue at the surgical site to deliver a gas below a surface of the surgical site to form a temporary pneumoperitoneum;

normalizing the pressure within the rigid dome;

separating a first dome portion from a second dome portion to remove the rigid dome from the surgical site with the medical apparatus remaining indwelling at the surgical site, wherein separating the first dome portion from the second dome portion comprises releasing a retaining band positioned on a band region extending around both the first dome portion and the second dome portion and dise saving a sealing element that removably seals a joining interface between the first dome portion and the second dome portion, wherein:

the rigid dome is further separated from the septum; and the septum remains attached to the medical apparatus after the rigid dome is removed from the surgical site; and removing the septum from the medical apparatus after the rigid dome is removed from the surgical site with the medical apparatus remaining indwelling at the surgical site.

9. The method of claim 8, wherein removing the septum from the medical apparatus comprises:

dividing the septum into a first septum portion and a second septum portion; and removing the divided septum from the medical apparatus with the medical apparatus remaining indwelling at the surgical site.

10. The method of claim 8, further comprising plugging the vacuum port to prevent pressure equalization through the vacuum port.

11. The method of claim 8, further comprising manipulating the rigid dome relative to the surgical site through an application of force at a raised structure extending from an exterior surface of the rigid dome.

12. A system, comprising:

a medical apparatus configured to be inserted at a surgical site;

a rigid dome configured to admit the medical apparatus through a septum into an interior of the rigid dome to allow the medical apparatus to be inserted at the surgical site, wherein:

the rigid dome is at least partially separable into a first dome section and a second dome section to remove the rigid dome from a surgical site without removing the medical apparatus from the surgical site;

the first dome section and the second dome section are joined at a joining interface;

the rigid dome further comprises a sealing element configured to removably seal the joining interface between the first dome section and the second dome section;

the rigid dome further comprises a retaining band configured to apply a retaining force to secure the first dome section relative to the second dome section, wherein the retaining band is positioned on a band region extending around both the first dome section and the second dome section:

the septum is separable from the rigid dome and remains attached to the medical apparatus as the first dome section and the second dome section are separated from each other;

wherein the septum further comprises grip tabs extending from the septum to form a location for gripping or dividing the septum, and the septum is at least partially divisible into a first septum portion and a second septum portion to remove the septum from the medical apparatus without removing the medical apparatus from the surgical site; and a vacuum source configured to connect to a vacuum port of the rigid dome to reduce a pressure within the rigid dome and raise tissue at the surgical site into the interior of the rigid dome for the insertion of the medical apparatus at the surgical site.

13. The system of claim 12, wherein the medical apparatus comprises a trocar for a laparoscopic surgical operation.

14. The system of claim 12, wherein the rigid dome further comprises:

a first retaining band positioned on a first band region formed on an exterior surface of the rigid dome; and a second retaining band positioned on a second band region on the exterior surface of the rigid dome, wherein the first retaining band and the second retaining band are configured to retain the rigid dome in a closed position and each of the first retaining band and the second retaining band are separable to facilitate at least partial separation of the rigid dome to remove the rigid dome from a surgical site without removing the medical apparatus from the surgical site.

15. The system of claim 12, wherein a material of the septum is different from a material of the rigid dome to allow for penetration of a medical apparatus into an interior of the rigid dome.

16. The system of claim 12, wherein the septum comprises a seal texture formed on the septum to provide a seal with the medical apparatus at the septum, wherein the seal texture is configured to provide a seal with a range of medical apparatus sizes.

17. The system of claim 12, wherein the first dome section of the rigid dome fully separates from the second dome section of the rigid dome.

18. The system of claim 12, wherein the first dome section and the second dome section are connected by a hinge, a tether, or a joint.

* * * * *